(12) United States Patent
Blomqvist et al.

(10) Patent No.: US 8,565,866 B2
(45) Date of Patent: Oct. 22, 2013

(54) METHOD AND DEVICE FOR MONITORING ACUTE DECOMPENSATED HEART FAILURE

(75) Inventors: Andreas Blomqvist, Spånga (SE); Nils Holmström, Järfälla (SE); Sven-Erik Hedberg, Kungsängen (SE); Malin Öhlander, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 434 days.

(21) Appl. No.: 12/809,255

(22) PCT Filed: Dec. 21, 2007

(86) PCT No.: PCT/SE2007/001155
§ 371 (c)(1),
(2), (4) Date: Jun. 18, 2010

(87) PCT Pub. No.: WO2009/082284
PCT Pub. Date: Jul. 2, 2009

(65) Prior Publication Data
US 2011/0144508 A1    Jun. 16, 2011

(51) Int. Cl.
*A61B 5/0295* (2006.01)
(52) U.S. Cl.
USPC .................. 600/547; 600/508; 600/506
(58) Field of Classification Search
USPC .................................. 600/506, 547
See application file for complete search history.

(56) References Cited

U.S. PATENT DOCUMENTS

| | | | |
|---|---|---|---|
| 4,562,843 A * | 1/1986 | Djordjevich et al. | 600/485 |
| 6,980,851 B2 * | 12/2005 | Zhu et al. | 600/513 |
| 7,082,329 B2 * | 7/2006 | Jarverud | 607/17 |
| 7,096,064 B2 * | 8/2006 | Deno et al. | 607/9 |
| 7,146,208 B2 * | 12/2006 | Holmstrom et al. | 600/547 |
| 7,395,114 B2 * | 7/2008 | Czygan et al. | 607/6 |
| 2005/0049646 A1 | 3/2005 | Czygan et al. | |
| 2007/0055170 A1 | 3/2007 | Lippert et al. | |
| 2007/0100249 A1 | 5/2007 | Torpo et al. | |
| 2007/0179390 A1 | 8/2007 | Schecter | |

OTHER PUBLICATIONS

"Acute Decompensated Heart Failure: A Contemporary Approach to Pharmacotherapeutic Management," McBride et al, Pharmacotherapy 23 (8), pp. 997-1020 (2003).
"Management of Acute Decompensated Heart Failure", Allen et al, Can. Med. Assoc. J. 176 (6), pp. 797-805 (2007).
"Diagnostic Monitoring Strategies in Heart Failure Management," Piccini et al, Am. Heart J. 156 (4), pp. 12-17 (2007).
"Usefulness of the Impedance Cardiogram to Reflect Left Ventricular Diastolic Function," Pickett et al, American Journal of Cardiology, vol. 71 (1993) pp. 1099-1103.

* cited by examiner

*Primary Examiner* — Joseph Stoklosa (57) ABSTRACT

An implantable medical device has an impedance determiner for determining a cardiogenic impedance signal based on electric signals sensed by connected electrodes. A parameter calculator processes the impedance signal to calculate an impedance parameter representative of the cardiogenic impedance in connection with the diastolic phase of a heart cycle. This parameter is then employed by the device for monitoring acute decompensated heart failure status of a subject.

24 Claims, 8 Drawing Sheets

METHOD AND DEVICE FOR MONITORING ACUTE DECOMPENSATED HEART FAILURE

BACKGROUND OF THE INVENTION

1. Field of the Invention

The present invention generally relates to monitoring of acute decompensated heart failure in subjects having an implantable medical device.

2. Description of the Prior Art

The heart is an essential organ in humans and most animals, pumping blood throughout the human/animal body. As a consequence, it is fundamentally important that the mechanical pumping properties of the heart operate correctly.

There are several diseases and conditions that negatively affect these mechanical properties of the heart. A severe such condition is acute decompensated heart failure (ADHF). This form of heart failure is characterized by the sudden inability of the heart to pump efficiently. However it is though not cardiac arrest because the heart does not stop though the heart pumping action significantly deteriorates.

The inability of the failing heart to pump blood in a forward direction creates a relative hypovolemic state known as arterial underfilling. As a response, several neurohormonal factors become activated to maintain euvolemia by causing fluid retention, vasoconstriction, or both. In the patient without heart failure, this response terminates once fluid volume has been restored. However, the activity of these systems remains chronically elevated in the patient with heart failure, thus contributing to the systemic and pulmonary congestion that are hallmarks of the disorder despite compensatory elevations in endogenous brain natriuretic peptide (BNP) levels. Neurohormonal activation also stimulates detrimental activation of pro-inflammatory cytokines and mediators of myocyte apoptosis. As reported in "Acute Decompensated Heart Failure: A Contemporary Approach to Pharmacotherapeutic Management," McBride et al, Pharmacotherapy 23(8), pp. 997-1020 (2003), elevations of many of the neurohormones and immunomodulators observed in patients with ADHF have been associated with a worsening of heart failure symptoms and a decline in the prognosis of the patients. Although these hormones are elevated in patients with compensated heart failure, their elevation can precipitate an episode of ADHF if they are not adequately suppressed by therapy.

Approximately 4.9 million people in the U.S. were diagnosed with ADHF in 2003. ADHF is the single most expensive hospital admission diagnosis according to the Center for Medicare and Medicaid Administration, with more than $3.6 billon spent in 1998 alone.

The success in treating ADHF patients and reducing the enormous cost associated with ADHF, is an early patient diagnosis. Today ADHF diagnosis is mainly limited to patient's history, physical examination, chest X-ray examination and laboratory tests. Characteristic of this prior art ADHF diagnosis is that it is time-consuming and cumbersome, often requiring dedicated X-ray and imaging facilities in addition to separate laboratory testing.

SUMMARY OF THE INVENTION

There is therefore a need for time-efficient and simpler ADHF detection that can be used in connection with at least a sub-portion of patients having a risk of developing ADHF or having a history of previous ADHF lapses. The present invention overcomes these and other drawbacks of the prior art arrangements.

It is a general object of the present invention to provide an implantable medical device having acute decompensated heart failure monitoring capability.

It is another object of the invention to provide a fast and simple acute decompensated heart failure detection and diagnosis indication.

Briefly, the present invention involves an implantable medical device (IMD) capable of monitoring acute decompensated heart failure (ADHF) status in a subject for the purpose of detecting an ADHF event or monitoring relapse from an ADHF event.

The invention is based on the discovery that the impedance associated with the subject's heart is fairly similar between healthy subject status and ADHF status during the systolic phase of a heart cycle. However, it was highly surprising that there are significant differences in the impedance between healthy and ADHF subjects in the diastolic phase of the heart cycle. Thus, by limiting or at least concentrating the impedance analysis to diastole, a much earlier and more reliable ADHF monitoring is obtained as compared to systolic impedance signals or total impedance signals over the whole heart cycle.

The IMD therefore has an impedance determiner adapted to determine an impedance signal associated with the subject's heart over at least a diastolic phase of a heart cycle. For this purpose the IMD has or is connected to at least two electrodes used for applying electric signals and measuring resulting electric signals to thereby be able to determine the impedance signal.

A parameter calculator of the IMD is provided for calculating an impedance parameter based on the determined impedance signal. This calculation involves applying a non-zero first weight to the impedance samples corresponding to diastole and applying a second smaller weight to the impedance samples from systole. In preferred embodiments, the first weight is one and the second weight is zero. This basically involves only utilizing the diastolic impedance samples or a portion thereof in the parameter calculation while omitting the systolic samples.

A monitor is arranged in the IMD for monitoring the ADHF status of the subject based on the calculated impedance parameter. This monitoring preferably involves a comparison of the impedance parameter with a reference parameter, where this reference parameter corresponds to a previously calculated impedance parameter or an average of multiple such previous impedance parameters.

An ADHF event or recovery of such an ADHF event is monitored through the parameter comparison. Such ADHF detection can then trigger compensating therapies by the IMD and/or generating alert messages urging a contact with medical personnel.

The present invention also involves a method of monitoring ADHF status using the diastolic impedance parameter of the present invention.

The invention offers the following advantages:

Allows ADHF detection and monitoring without the need for extensive tests and examination at healthcare facilities;

Increased specificity and reliability in ADHF monitoring;

Provides an early detection of ADHF events; and

Can initiate compensating treatment directly upon ADHF detection.

Other advantages offered by the present invention will be appreciated upon reading of the below description of the embodiments of the invention.

DESCRIPTION OF THE PREFERRED EMBODIMENTS

Throughout the drawings, the same reference characters will be used for corresponding or similar elements.

The present invention is generally related to monitoring the status of acute decompensated heart failure (ADHF) in patients, including human and animal patients, having an implantable medical device (IMD). The present invention teaches an impedance-based ADHF monitoring that allows for an early detection of a sudden change in ADHF status, such as a detection of ADHF, and also a more reliable ADHF status monitoring. The present invention achieves this early and reliable monitoring by limiting or concentrating the analysis of the impedance signal to a selected portion of a heart cycle or beat.

The invention is based on the discovery that changes in ADHF status can be more accurately followed by analyzing the change in impedance signal associated the patient's heart during the diastolic phase of the heart cycle. Early indications of ADHF, ADHF relapse and recovery from ADHF are much more clearly evident in the diastolic portion of the impedance signal as compared to the systolic portion.

This finding was very surprising as the general belief is that heart failure, possibly with the exception of diastolic heart failure, mainly affects the systolic phase of the heart cycle. As a consequence, prior art impedance-based heart failure detection schemes have been using only the systolic impedance portion or the impedance signal during the whole heart cycle.

However, by limiting or concentrating the analysis to the interesting portion of the impedance signal, the present invention will detect even minor changes in the impedance signal that are due to a change in ADHF status. Such minor changes are not detectable in the systolic phase or would be regarded as baseline variations if the impedance signal during the whole heart cycle was instead used. Furthermore, changes in the impedance signal due to a change in ADHF status first occurs in the diastolic heart cycle phase. It is first when ADHF has been present for some time that impedance changes become detectable even in the systolic phase. The present invention therefore provides an earlier ADHF detection by limiting or concentrating the impedance monitoring to the diastole.

The early ADHF detection of the present invention significantly improves the chances of successful treatment and recovery from the ADHF condition as the time of diagnosis strongly affects the outcome of any ADHF treatment. The invention therefore provides advantages to both IMD patients and to the society in large by having a possibility of reducing the hospitalization periods and costs due to the early ADHF detection.

Traditionally, there is a significant risk of sending home patients having been treated for ADHF as these patients seem to have fully recovered from the ADHF condition. However, several of the patients have though not stably recovered from the condition and may therefore soon have to visit a physician due to ADHF relapse. The present invention can be of advantage also for these patients as the diastolic-based impedance analysis of the invention can be used for monitoring the ADHF recovery status. As a consequence, premature declaration of fit may be reduced.

Figure 1:
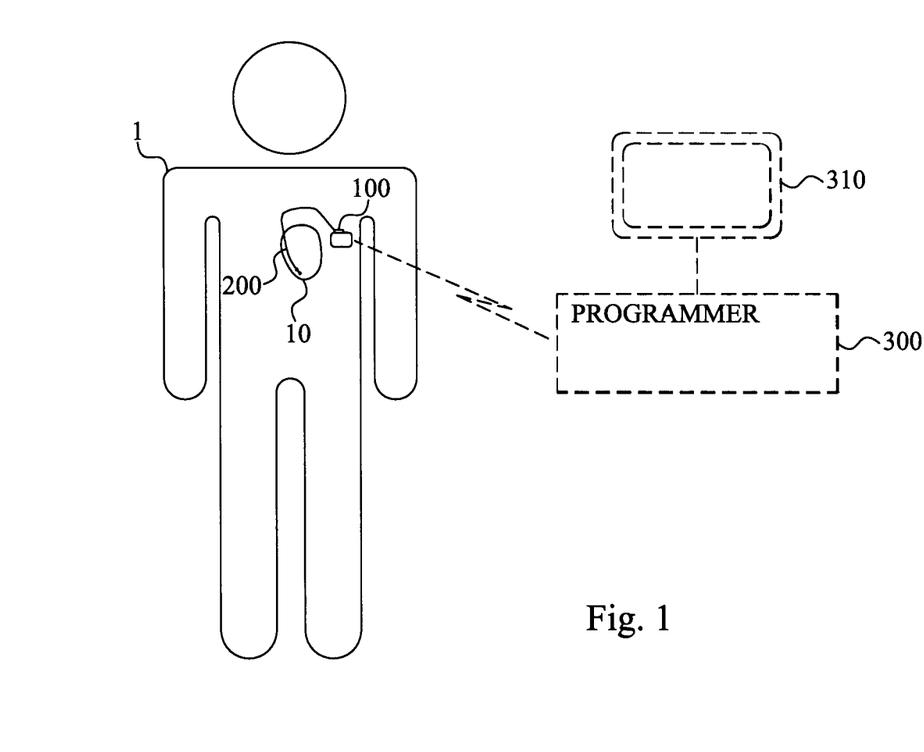
FIG. 1 is a schematic overview of a patient having an implantable medical device according to the present invention and an external unit capable of conducting communication with the implantable medical device.

FIG. 1 is a schematic overview of a patient 1 having an implantable medical device, IMD, 100 according to the present invention. In the figure, the IMD 100 is illustrated as a device that monitors and/or provides therapy to the heart 10 of the patient 1, such as a pacemaker, cardiac defibrillator or cardioverter. The IMD 100 is, in operation, preferably connected to one or more cardiac leads 200, including intracardiac leads inserted into a heart chamber (right ventricle in the figure) and/or endocardial leads.

Though, the IMD 100 preferably has at least one electric lead 200 equipped with impedance sensing electrodes, the present invention can also be used with IMDs 100 not equipped with cardiac leads as long as the IMD 100 has or is connectable to at least two electrodes used for sensing electric signals for the purpose of calculating an impedance signal used in the ADHF monitoring of the present invention. In such a case, the IMD 100 could contain at least two electrodes. Alternatively, the IMD 100 comprises at least one electrode, while at least one other electrode is positioned on the lead(s) 200. In a further embodiment, all electrodes are situated in one or more leads 200.

As is well known in the art, impedance measurement can be conducted using bipolar, tripolar or quadropolar measurements. In the first case, an electric signal (current or voltage signal) is applied using two electrodes, which are also employed for sensing the resulting electric signal (voltage or current signal). In tripolar measurement, the electric signal is applied using two electrodes, and the resulting electric signal is sensed over two electrodes of which one was used in the signal application. Finally, quadropolar measurements use a first set of two electrodes for signal application and a second set of two different electrodes for signal sensing. The present invention can be used in connection with any of these bipolar, tripolar or quadropolar measurements.

Furthermore, the invention can be used in connection with different impedance vectors (depends on the particular placement of the applying and sensing electrodes). The basic feature is that the resulting impedance signal that is determined based on the applied and sensed signals contains a contribution from impedance changes from the heart. As a consequence, a preferred impedance signal according to the present invention can be the so-called cardiogenic impedance signal, which is generally obtained by filtering a raw impedance signal to enhance cardiac frequencies/activities. A typical example could be the usage of a bandpass filter of 0.32-64 Hz.

FIG. 1 also illustrates an external programmer or clinician's workstation 300 that can communicate with the IMD 100. As is well known in the art, such a programmer 300 can be employed for transmitting IMD programming commands causing a reprogramming of different operation parameters and modes of the IMD 100. Furthermore, the IMD 100 can upload diagnostic data descriptive of different medical parameters or device operation parameters collected by the IMD 100. Such uploaded data may optionally be further processed in the programmer 300 before display to a clinician on a connected display screen 310. In the light of the present invention, such diagnostic data can include impedance data measured by the IMD 100 and/or other diagnostic data relating to ADHF status monitoring and detection.

In the present invention, ADHF status is monitored to detect any changes in the ADHF status based on the impedance signal analysis. The expression "ADHF status" covers getting AHDF, relapse of ADHF but also recovery from ADHF.

Figures 2, 4:
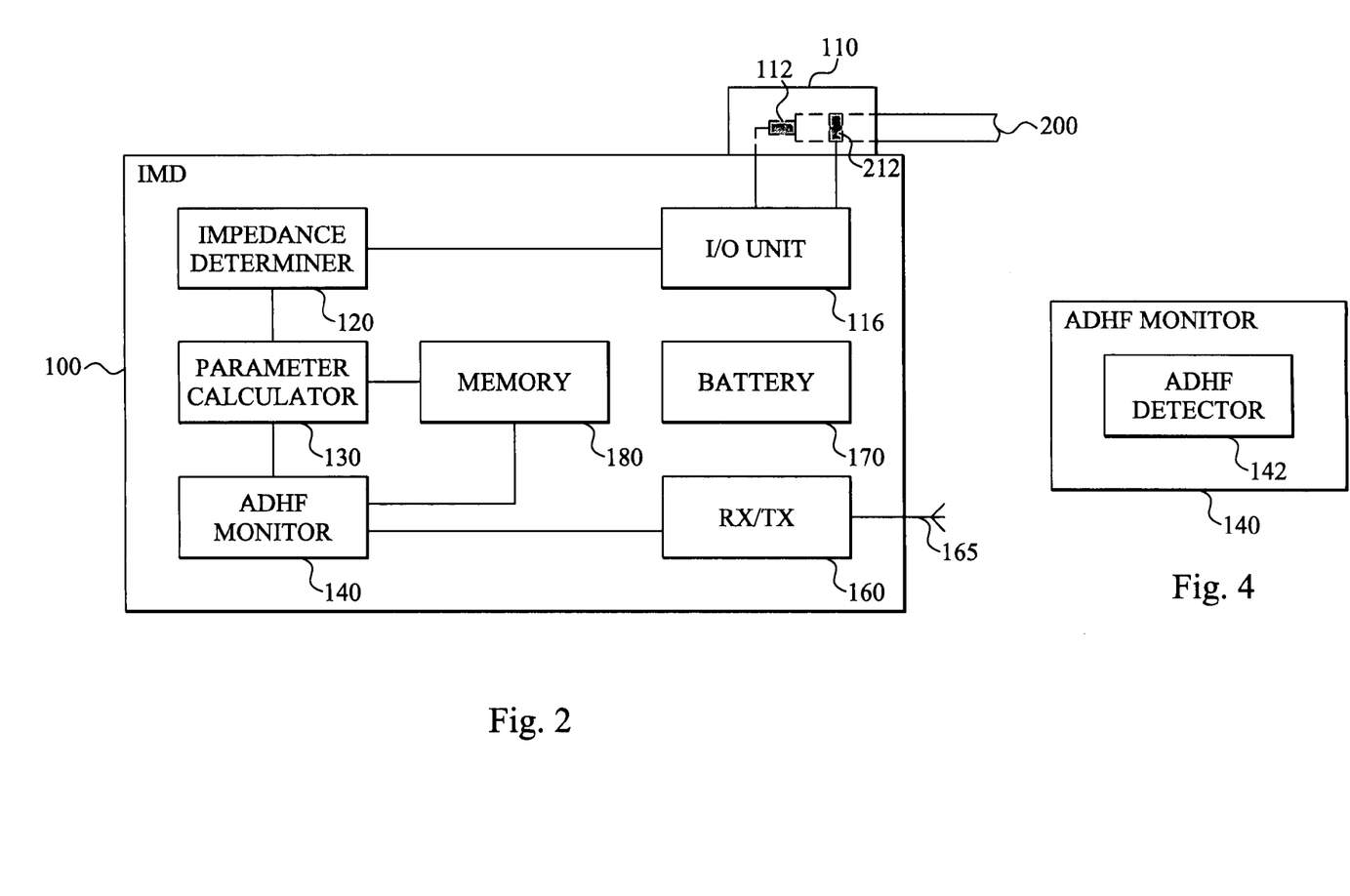
FIG. 2 is a schematic block diagram of an embodiment of an implantable medical device according to the present invention.
FIG. 4 is a schematic block diagram on an embodiment of the ADHF monitor of FIGS. 2 and 3.

FIG. 2 is a schematic block diagram of an IMD 100 according to the present invention. The IMD 100 comprises an electrode connecting arrangement 110 arranged in the IMD 100 for providing a connection unit to the at least two electrodes used for the impedance measurements of the present invention. In a typical implementation, the connecting arrangement 110 is, in operation, connectable to a proximal end of an implantable electric lead 200 having at least two electrodes in connection with its opposite distal end, such as a helical/tip electrode and at least one ring electrode. The lead 200 houses conductors running through the lead body length to provide electrical contact between the electrode(s) at the distal end with electrode terminals 212 at the distal end. The connecting arrangement 110 then exhibits matching terminals 112 that are in electric contact with the electrode terminals 212 of the lead 200 to thereby provide an electric connection between the distal electrodes and the IMD 100.

The connecting arrangement 110 can, as has been described above, be connectable to one or more such implantable electric leads positioned at different anchoring sites in the subject body, such as at different cardiac positions (different heart chambers and/or intracardial versus endocardial positions).

The present invention is though not limited to lead-carrying electrodes. In clear contrast, one of the electrodes could be the can or case, i.e. housing, of the IMD 100 itself. Furthermore, dedicated electrodes that are not positioned on cardiogenic leads could also be used and are then connected to the arrangement 110.

An input/output (I/O) unit 116 is preferably arranged in the IMD 100 for providing an interface between the connecting arrangement 110 and the IMD units, in particular an impedance calculator or determiner 120. This determiner 120 is adapted to determine an impedance signal associated with the heart of the subject based on electric signals sensed by the electrodes connected to the connecting arrangement 110. The impedance signal reflects the impedance changes of the heart, or at least a portion thereof, such as a heart chamber, during at least a diastolic phase of a heart beat. Thus, the impedance signal can be recorded over multiple subsequent heart beats, over a single heart beat or over an interval of a heart beat as long as the interval covers a major portion of the diastolic phase.

A parameter calculator 130 is arranged connected to the impedance determiner 120 and is adapted to process and analyze the determined impedance signal for the purpose of calculating a diagnostic impedance parameter. The calculator 130 generates the parameter by applying a non-zero first weight to a diastolic portion of the impedance signal corresponding to at least a portion of the diastolic phase of the heart beat and applying a second weight to a non-diastolic (systolic) portion of the impedance signal. The key concept of the invention is that the first weight is larger than the second weight.

In a particular embodiment of the present invention, the first weight is one and the second weight is zero. This means that the calculator 130 only utilizes the portion of the impedance signal corresponding to diastole for calculating the impedance parameter. Any impedance samples corresponding to the remaining portion of the heart beat, basically systole, are simply ignored or omitted from the calculation. Such an isolated impedance analysis of the impedance signal generates a diastolic impedance parameter representative of the cardiogenic impedance during the diastolic phase.

Even though a strictly diastolic analysis of the impedance signal provides a cleaner diastolic impedance parameter, the calculator 130 can alternatively also use one or more impedance samples from the systolic heart cycle phase. However, in such a case, these samples should be weighted lower than corresponding samples from diastole. The impedance parameter will then concentrate on the diastolic phase even though there is a (small) contribution from non-diastolic impedance samples.

The present invention can therefore be used in connection with calculators 130 that are able to identify only those impedance samples from the determiner 120 that corresponds to diastole and calculators 130 that use all or at least a majority of the impedance samples from the determiner but then applies different weights to the samples to get a comparatively larger contribution from the diastolic impedance samples.

The parameter calculator 130 is preferably connected to a memory 180, in which the calculated impedance parameter can be stored for later use. The parameter calculator 130 is also connected to an ADHF monitor 140. The calculator 130 then forwards the calculated impedance parameter directly to the monitor 140 or the monitor 140 can fetch it from the memory 180. In either case, the monitor 140 is adapted to monitor the ADHF status of the subject based on the impedance parameter. The monitor 140 analyzes the received or fetched impedance parameter to detect any significant changes in the parameter, which changes are due to changes in the ADHF status of the subject. For instance, the monitor 140 can detect an acute decompensated heart failure event in the subject based on the parameter analysis. The monitor 140 can also detect such an ADHF relapse in a subject having a history of ADHF events. However, the impedance parameter of the invention is not only limited to usage in ADHF diagnosis but is also of highly valuable use for monitoring recovery of a previous ADHF event, which is described further herein.

The ADHF monitor 140 preferably generates a representation of the monitored ADHF status based on the impedance parameter. This representation can specify a warning of an emergent ADHF event, contain information of the ADHF recovery status of an ADHF patient or basically specifying that the ADHF status is normal, i.e. no ADHF event. The representation can also or alternatively contain more detailed information, such as information of a difference between a currently determined impedance parameter with a standard or reference parameter representing a healthy subject status. Such a difference can then be a representation of an eminent ADHF event, how severe a current ADHF event is or the ADHF recovery status.

The IMD 100 also comprises a transmitter and receiver 160 with connected antenna 165. This unit 160 is employed by the IMD 100 for conducting wireless uni- or bidirectional communication with an external unit, such as the programmer in FIG. 1. The transmitter portion of the unit 160 is in particular suitable for forwarding the impedance parameter from the calculator 130 or monitor 140 or forwarding the ADHF status representation from the monitor 140 to the external unit. At the external unit a physician can use the parameter or representation for diagnostic purposes.

A battery 170 is arranged in the IMD 100 for providing the required power supply to the including IMD units.

The units 116, 120, 130, 140, 160 of the IMD 100 can be implemented in hardware, software or a combination of hardware and software.

Figure 3:
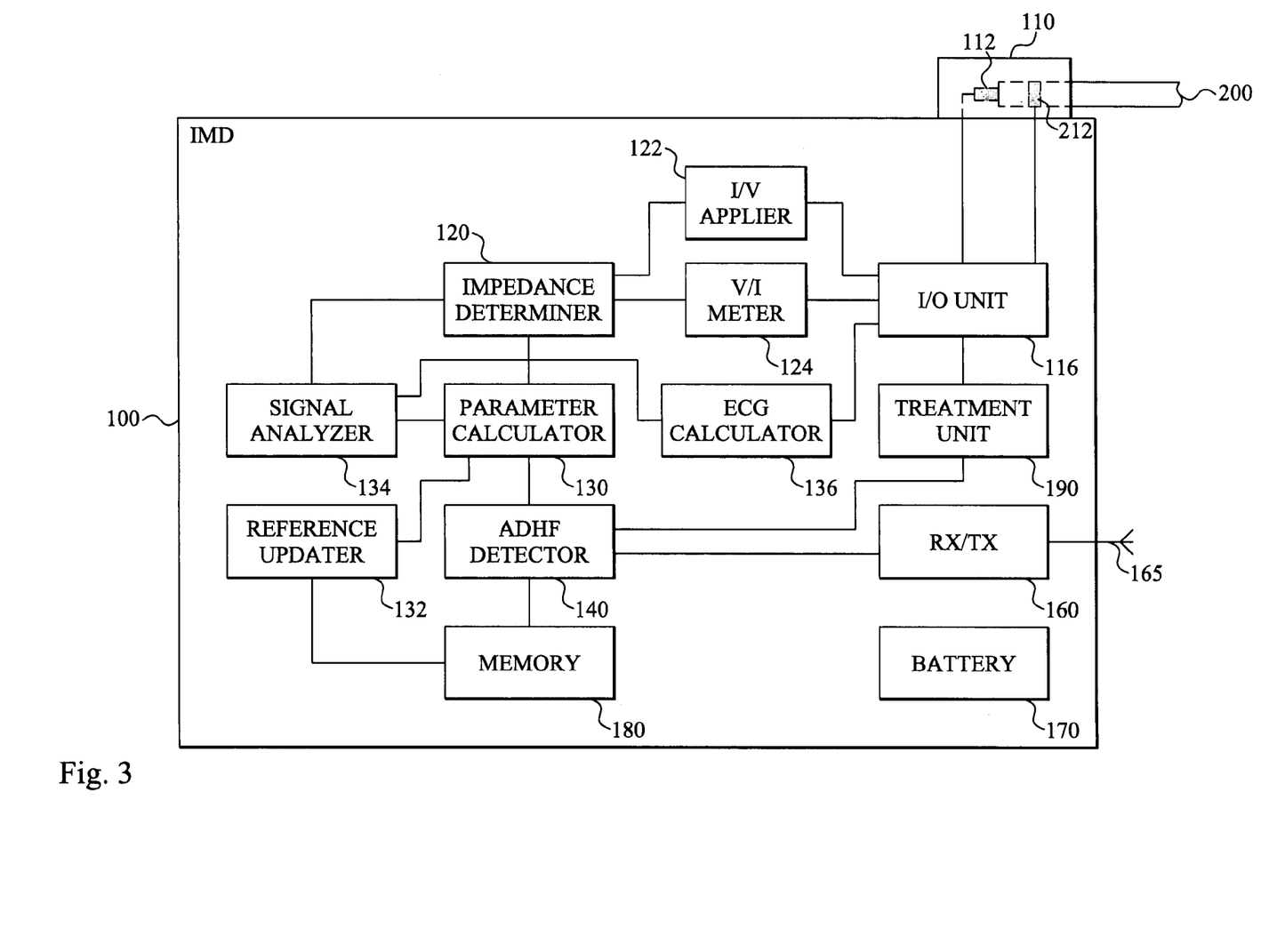
FIG. 3 is a schematic block diagram of another embodiment of an implantable medical device according to the present invention.

FIG. 3 is a schematic block diagram of a more detailed implementation embodiment of the IMD 100. The IMD 100 comprises an electric signal applier 122 connected to the electrodes through the I/O unit 116, terminals 112, 212 and the electric lead 200 in the figure. This signal applier 122 is arranged for applying a (AC) current or voltage signal through two electrodes to at least a portion of the heart. The signal application is at least performed during a diastolic phase of a heart beat but can alternatively be applied over a whole heart cycle or multiple subsequent cycles.

A signal measurer 124 is likewise connected to two electrodes through the I/O unit 116 and the terminals 112, 212 in the connecting arrangement 110. The measurer 124 measures a resulting (AC) voltage or current signal sensed by two electrodes connected to the IMD 100. As was discussed in the foregoing, these two sensing electrodes can be the same as the electrodes used for signal application (bipolar configuration), one electrode can be common between signal application and sensing (tripolar configuration) or dedicated sensing and application electrodes can be used (quadropolar configuration). The measurer 124 is adapted to measure the resulting voltage (or current) signal at least during diastole but typically gets voltage (or current) sample through a whole heart cycle or even multiple heart cycles.

The impedance determiner 120 is connected to the signal applier 122 and measurer 124 and calculates the impedance signal based on the applied current (or voltage) signal and the measured resulting voltage (or current) signal according to known techniques. In a preferred embodiment, the impedance signal is determined as an average signal over multiple consecutive heart beats, preferably synchronized to each QRS. Such a signal averaging smoothes out temporary deviations that can occur during a single heart beat for various reasons. In such a case, an average of 2 to 20 consecutive heart beats is generally advantageous in the impedance signal determination.

The parameter calculator 130 can use different techniques for identifying the interesting portion of the impedance signal from the determiner 120, i.e. the portion of the (averaged) impedance signal corresponding to diastole. In a first embodiment, this interesting diastolic portion corresponds to the time period following closure of the aortic valve up to atrial contraction. If non-zero weights are used for both diastolic and non-diastolic impedance signal portions, the larger first non-zero weight is applied to the impedance samples corresponding to the above described time period while impedance samples falling outside of the time interval are multiplied by the smaller second weight. Otherwise the impedance samples occurring outside of the interesting time interval are simply removed from the processing.

The interesting heart cycle portion as defined according to above can be determined by a physician and then be programmed into the IMD 100. Thus, the parameter calculator 130 then has access to information, such as time or sample information, allowing identification of the interesting portion from aortic valve closure up to atrial contraction based on some time or sample reference that is easily identifiable in the impedance signal, such as the QRS complex.

In another embodiment, the parameter calculator 130 only uses or at least concentrates the parameter calculation on the impedance signal samples falling inside the time interval consisting of isometric relaxation and rapid filling of the ventricles of the heart during diastole. This interval can be identified according to techniques similar to what is described above.

Figure 5:
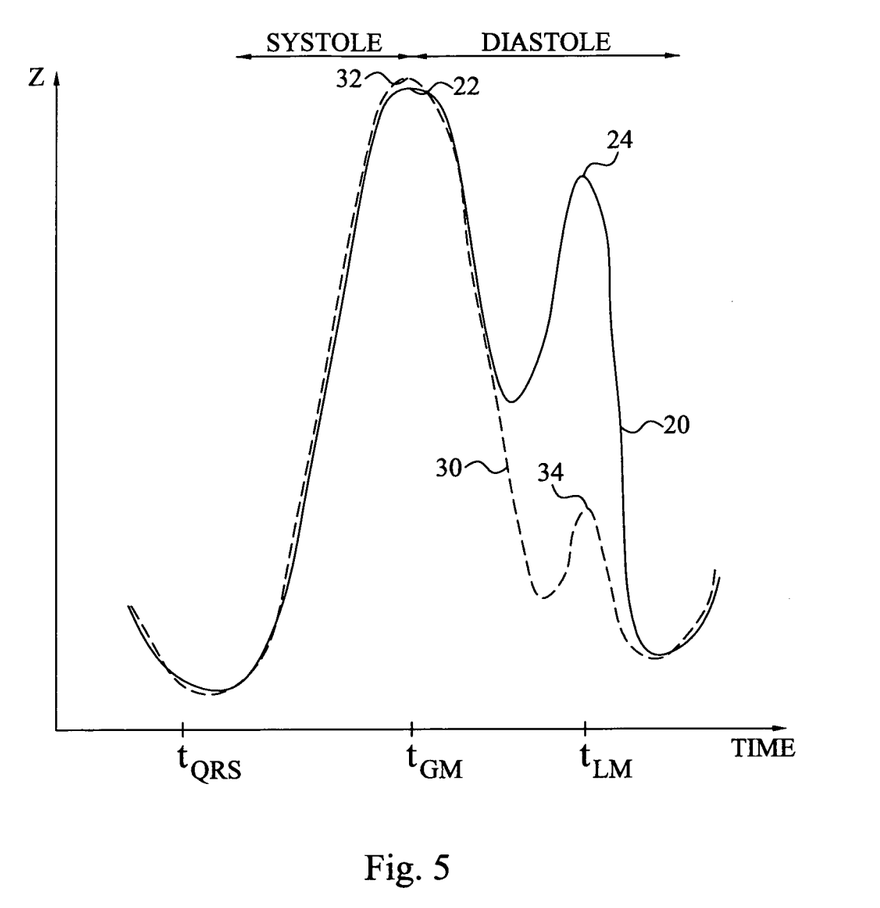
FIG. 5 is a diagram schematically illustrating a difference in impedance signal from a healthy subject and the subject suffering from ADHF.

A signal analyzer 134 can be implemented in the IMD 100 and used by the calculator 130 for identifying the interesting diastolic part of the impedance signal. FIG. 5 is a diagram illustrating an example of the changes in cardiogenic impedance 20, 30 measured over a heart cycle, i.e. including both systole and diastole. With reference to both FIGS. 3 and 4, the signal analyzer 134 preferably is configured for identifying a first local maximum 24, 34 in the impedance signal occurring in the diastolic phase. This identification can be realized by first identifying the global maximum 22, 32 in the impedance signal during a heart beat. This global maximum typically corresponds to the transition from systole to diastole. The first local maximum 24, 34 in diastole is then identified as the first local maximum occurring following the identified global maximum 22, 32. The signal analyzer 134 can then utilize well-known techniques for identifying global/local maximums in a signal, which is a straightforward task for the person skilled in the art.

The parameter calculator 130 identifies the interesting portion from ADHF point of view as the portion of the impedance signal corresponding to this peak in the diastole, i.e. from the start of peak to the end of the peak or some later time period in diastole.

Test studies have been conducted to and used for determining the onset of the diastole part of the impedance signal following an identified QRS complex. As a consequence, the signal analyzer 134 can perform processing of the impedance signal to identify, for a given heart cycle, such a QRS complex. The diastolic phase is then determined as occurring following a predefined time period, preferably about 300-500 ms, such as about 400 ms, from the QRS complex up to the end of the diastolic phase, such as the occurrence of the QRS complex in the next heart cycle.

Even though the QRS complex can be identified by the signal analyzer 134 from the impedance signal, an electrocardiogram is typically a better source for QRS identification. As a consequence, the IMD 100 preferably comprises an electrocardiogram calculator 136 connected to sensing electrode(s), preferably attached to implantable cardiac leads 200. The calculator 136 then uses the paced or intrinsic electric cardiogenic signals for determining an electrocardiogram signal. The signal analyzer 134 is connected to and receives the electrocardiogram signal from the calculator 136. The analyzer 134 processes the received signal to identify the timing of such a QRS complex during a heart cycle. In this embodiment, the impedance signal and the electrocardiogram signals are preferably synchronized or time marked using an internal clock (not illustrated). This means that the two signals are recorded in a same or matching time frame.

The parameter calculator 130 identifies relevant period of the impedance signal based on the occurrence of the QRS complex in the electrocardiogram signal. As described above, this interesting portion is from about 300-500 ms, such as about 400 ms following the timing of the QRS complex up to the end of diastole.

There are several different parameters that the parameter calculator 130 could generate and that are suitable for ADHF monitoring purposes. With reference to FIG. 5, a suitable impedance parameter could be representative of a time difference between the occurrence of the global maximum 22, 32, i.e. $t_{GM}$, and the first local maximum 24, 34 in diastole, i.e. $t_{LM}$. Another suitable parameter is generated based on the amplitude of impedance signal in connection with the global maximum 22, 32 and the first local maximum 24, 34 in diastole. The parameter could then be a quotient of the impedance values at the two peaks 22, 32; 24, 34 or a difference between the impedance values.

Another suitable impedance parameter is a representation of a time difference between the occurrence of the QRS complex, i.e. $t_{QRS}$, and the first local maximum 24, 34 in diastole, i.e. $t_{LM}$.

The area under the impedance curve 20, 30 during diastole or one above-described interesting portions of diastole is also a suitable impedance parameter of the invention. The parameter calculator 130 then performs an integration calculation according to techniques known in the art to get an estimate of the area under the impedance curve 20, 30 in diastole.

A further example is to perform a line integration of the impedance curve 20, 30 during diastole. The impedance parameter is then representative of the length of the impedance curve 20, 30 during this interesting phase of the heart cycle. Algorithms for performing line integration are well-known in the art.

A further example includes parameters representative of the curvature of the first local maximum 24, 34 in diastole.

Thus, there is vast amount of different impedance parameters that can be used according to the present invention and the above-listed ones should merely be seen as preferred but non-limiting examples. The important feature is not what particular parameter to use but that the selected parameter reflects and is representative of the impedance signal during diastole. It is anticipated by the present invention that the parameter calculator 130 can calculate more than one impedance parameter per received (average) impedance signal. In such a case, the ADHF monitor 140 preferably uses these different impedance parameters in the ADHF status monitoring.

FIG. 4 is a schematic block diagram of a preferred embodiment of the ADHF monitor 140 of FIGS. 2 and 3. The monitor 140 comprises an ADHF detector 142 that is arranged for detecting ADHF or ADHF relapse or recurrence in the subject based on the impedance parameter. In a preferred implementation, the detector 142 performs this ADHF detection based on a comparison of the determined (average) impedance parameter(s) with at least one reference parameter. This reference parameter can then be fetched from the memory 180 illustrated in the IMDs 100 of FIGS. 2 and 3.

The reference parameter is of a same parameter type as the determined impedance parameter. Thus, if the impedance parameter is indicative of the area under the impedance curve during diastole, the reference parameter is then a corresponding area measure associated with a healthy non-ADHF subject status. This means that if multiple different impedance parameters are calculated by the parameter calculator 130, the memory preferably has at least one such reference parameter per parameter type.

The reference parameter can be a standard parameter that is hard coded in the IMD during manufacture or the standard parameter can be received by the IMD receiver 160 following implantation into the subject body. In such a case, the programmer or some other external communications unit downloads the standard parameter into the IMD memory 180. Such a standard parameter is then preferably generated based on recordings collected from a multitude of healthy subjects, i.e. as an average of these different recordings. By utilizing impedance measurements during diastole from several different healthy IMD subjects, individual variations in the impedance signal will be smoothed out.

However, the impedance signal is highly dependent on the particular impedance vector utilized, the positioning of the signal applying and sensing electrodes and also varies from patient to patient. In a preferred embodiment, the reference parameter is therefore based on previous recording conducted by the IMD 100 on the same patient. This means that a subject-specific impedance parameter comparison is utilized by the ADHF detector 142, thereby increasing the specificity in the ADHF detection significantly as compared to standard parameters.

The parameter comparison performed by the ADHF detector 140 is preferably based on calculating a difference between the impedance and the reference parameter. If this difference exceeds a defined threshold parameter, e.g. stored in the memory 180, the detector 142 concludes that ADHF is detected. Alternatively, a quotient between the impedance and the reference parameter could alternatively be calculated and compared to a defined threshold.

If the determined impedance parameter does not significantly deviate from the reference parameter, the reference parameter can be updated by a reference updater 132 based on the impedance parameter. Thus, the updater 132 calculates an updated reference parameter based on the impedance parameter and the previous reference parameter, such as an average or weighted average.

In the case of a significant difference between the reference and impedance parameters, the ADHF detector may store information of the difference and/or the impedance parameter in the memory 180. A physician can then upload this diagnostic information for medical evaluation.

Furthermore, the ADHF detector 142 in the monitor 140 can be connected to an ADHF treatment unit 190 provided in the IMD 100 combating a detected ADHF event through application of pacing pulses according to a defined anti-ADHF scheme using the connected cardiogenic leads 200. As a consequence, ADHF treatment can be initiated directly following its early detection according to the invention, thereby significantly improving the chances of a fully recovery. In such an embodiment, treatment can be initiated directly once ADHF has been detected by the detector 142 even though the subject is not present in any healthcare facility.

The detector 142 can also advantageously generate an alert message, optionally including information of the determined impedance parameter or the difference between it and the reference parameter, upon ADHF detection. That message can be immediately sent by the transmitter 160 to an external unit, whether it is the physician's programmer or a portable IMD-communicating device worn by the subject. Such an alert will urge the subject to immediately visit a physician unless already present in a healthcare facility.

In order to provide a reliable confirmation of the presence of ADHF, the impedance parameter is preferably determined based on the diastolic cardiogenic impedance for several consecutive heart cycles. Alternatively, or in addition, ADHF is confirmed by the detector 142 if a significant difference exists between the reference parameter and impedance parameters determined at multiple independent but following measurement instances. Thus, ADHF could be confirmed by the detector 142 if there is a significant difference between the impedance and reference parameter for N following measurement instances, where N is some predefined integer larger than one.

The IMD 100 of the present invention can also be utilized as a valuable tool when monitoring the recovery from an ADHF event. The ADHF recovery status can then be determined by the ADHF monitor 140 based on a comparison of the reference parameter and impedance parameters calculated from raw impedance data from different time instances. The recovery can then be followed by monitoring the difference between the reference and impedance parameters, which difference should preferably be smaller and smaller as the recovery is progressing. A subject can then be regarded as fully recovered when the difference between the reference parameter and the impedance parameter is insignificant or at least smaller than a minimum threshold. In order to obtain a reliable recovery detection, the difference should preferably be insignificant or smaller than the minimum threshold for at least multiple consecutive monitoring occasions as discussed above in connection with ADHF detection.

The IMD 100 preferably performs impedance measurements at multiple different time instances. Thus, the current/voltage applier 122 can be configured for intermittently or periodically applying, through the connected electrodes, a current or voltage signal to allow the voltage/current measurer 124 to measure a resulting voltage/current signal for the purpose of determining the impedance signal. For instance, the impedance signal can be determined once every hour, or even more often. However, for most practical implementations it may be enough to measure the cardiogenic impedance one or a limited number of times per day, per week or even more seldom.

The units 116, 122, 24, 20, 130, 132, 134, 136, 140, 142, 160 and 190 of the IMD 100 can be implemented in hardware, software or a combination of hardware and software.

FIG. 5 is a diagram schematically illustrating a difference in impedance signal recorded over a heart cycle for a healthy subject, impedance curve 24, and at a later occasion where the subject is suffering from ADHF, impedance curve 34. As can be seen from the FIG. 5, there is only minor differences in the impedance signals 24, 34 during the systole phase of the heart cycle, while the two curves 24, 24 differs significantly during diastole. This is the basis for the diastolic impedance analysis of the present invention.

Figure 6:
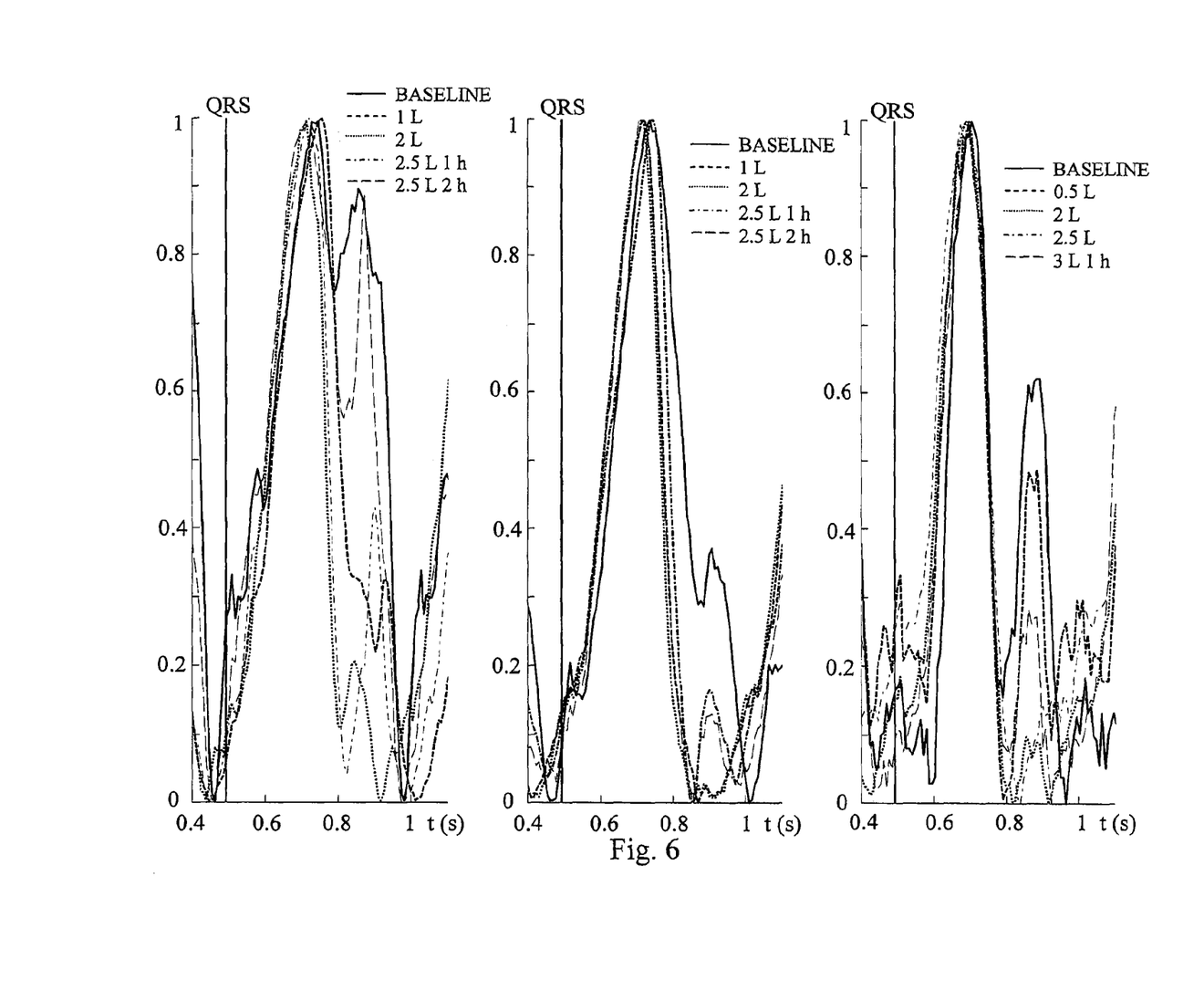
FIG. 6 illustrates diagrams of amplitude-normalized impedance signals changes in three animal subjects from an exacerbation volume overload provocation using bipolar impedance measurements between tip and ring electrode of a right ventricular lead.

FIG. 6 illustrates diagrams of amplitude-normalized impedance signals changes in three canine subjects from an exacerbation volume overload provocation using bipolar impedance measurements between tip and ring electrode of a right ventricular lead. In this study, the animals have been exposed to rapid pacing for a couple of weeks. This causes chamber dilation, mechanical dyssynchrony and decreased systolic function. Once heart failure has been verified, the subjects are exposed to an acute volume overload provocation where bags of saline solution are infused in their systems to cause acute fluid congestion. In FIG. 6, the curve baseline represents the impedance signal before infusion of saline solution. The curves 1 L, 2 L and 2.5 L are after infusion of one, two and two and a half liters, respectively. Finally, the curves 2.5 L 1 h, 2.5 L 2 h and 3 L 1 h are the impedance signals one or two hours after infusion of 2.5 liters or 3 liters.

As can be seen in all experiments, after normalization of the impedance signal (to get rid of amplitude variations), there are significant morphological variations in the impedance signal appearing in the same relative position during the diastolic phase of the heart cycle. This variation occurs about 400 ms after the QRS in the heart cycle.

Figure 7:
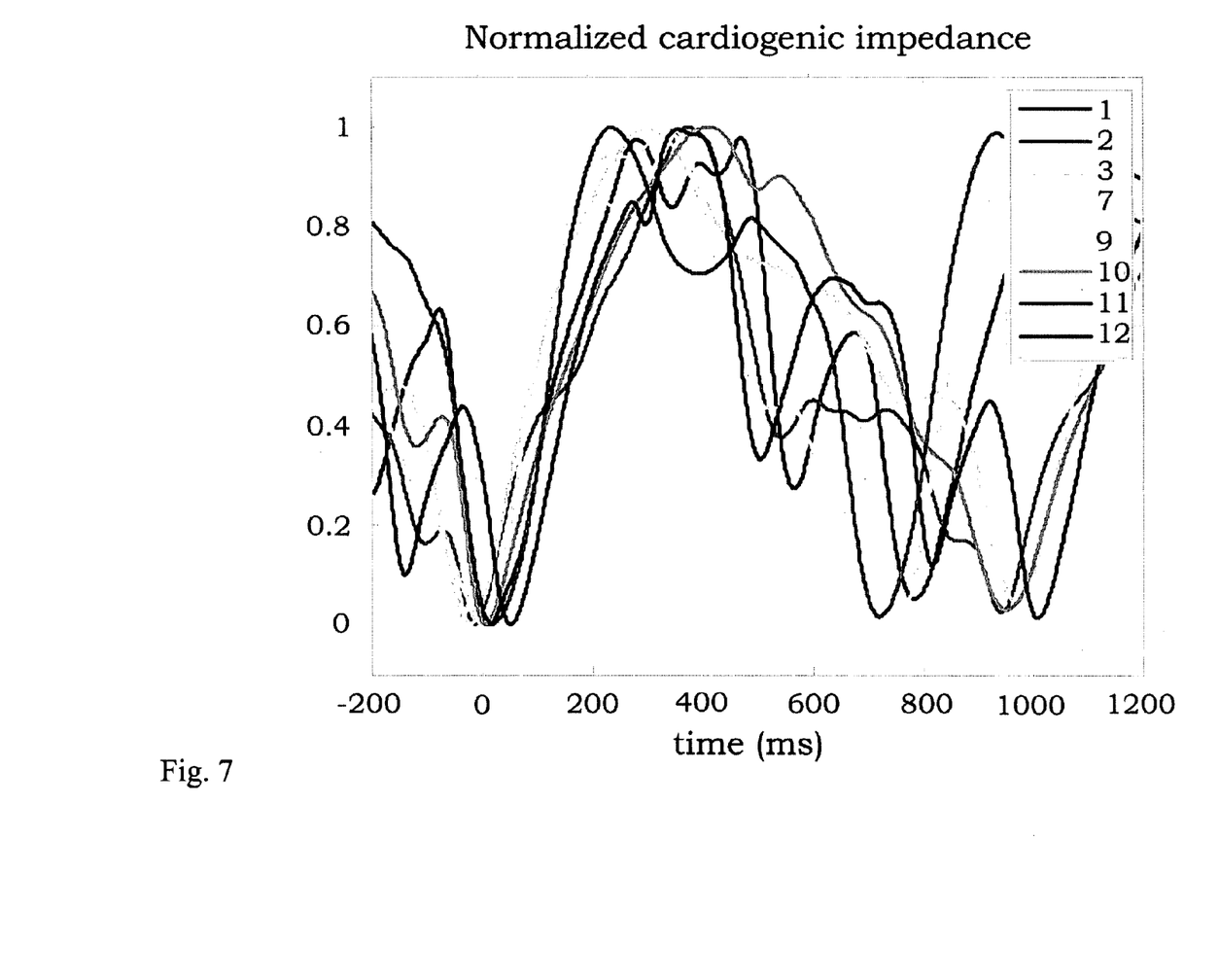
FIG. 7 is a diagram of amplitude-normalized impedance signals from human subjects at different stages of heart failure using quadropolar impedance measurements by applying a current signal between a tip electrode of a right ventricular lead and the case and measuring the resulting voltage between a ring electrode of the right ventricular lead and an electrode of a unipolar left ventricular lead.

FIG. 7 is a diagram of amplitude-normalized impedance signals from human subjects at different stages of heart failure using quadropolar impedance measurements by applying a current signal between a tip electrode of a right ventricular lead and the case and measuring the resulting voltage between a ring electrode of the right ventricular lead and an electrode of a unipolar left ventricular lead. FIG. 7 clearly illustrates that there are only minor differences in the normalized impedance signals during systole (corresponds to 0 to up to about 400 ms in the diagram). However, there is a significant variation in the impedance signal in the following diastolic phase.

Taken together these experimental results support the inventive concept of the invention that variations in impedance signal first and above all occur in the diastolic phase of the heart cycles. The ADHF monitoring and detection of the present invention is based on this finding by limiting or at least concentrating the analysis of the impedance signal to this interesting diastolic phase.

Figure 8:
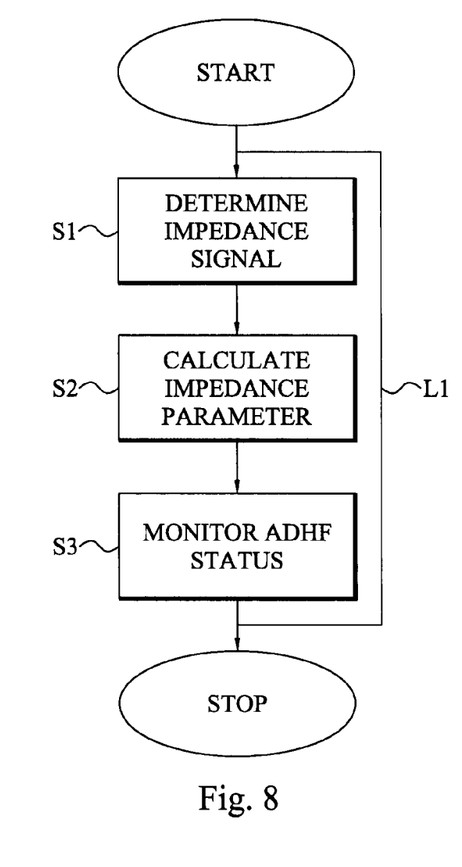
FIG. 8 is a flow diagram of a method of detecting ADHF according to an embodiment of the present invention.

FIG. 8 is a flow diagram of a method of monitoring ADHF status in an animal subject, preferably mammalian subject and more preferably human subject. The method starts in step S1 that involves determining an impedance signal representative of the impedance associated with the subject's heart over at least a diastolic phase of a heart beat. An impedance parameter is calculated in step S2 based on the determined impedance signal. This calculation involves applying a non-zero first weight to a diastolic portion of the impedance signal and applying a second weight to the non-diastolic portion of the impedance signal. In a preferred embodiment the first weight is one and the second weight is zero. This basically involves only processing the impedance samples originating from diastole while ignoring the other, such as systolic, samples.

A next step S3 monitors the ADHF status in the subject based on the calculated impedance parameter.

The monitoring method of steps S1 to S3 is preferably performed at multiple different time instances, such as periodically or intermittently, which is schematically illustrated by the line L1.

Figure 9:
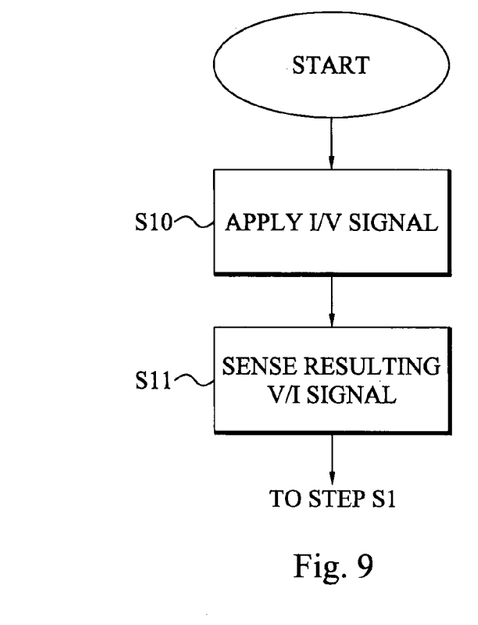
FIG. 9 is a flow diagram of additional steps of the ADHF detecting method in FIG. 8.

FIG. 9 is a flow diagram illustrating additional steps of the monitoring method of FIG. 8. Step S10 involves applying a current or voltage signal using two electrodes to at least a portion of the subject's heart. Two electrodes are correspondingly used in step S11 for sensing or capturing the resulting voltage or current signal. The impedance signal is then determined based on the sensed voltage (current) signal and based on information of the applied current (voltage) signal in step S1 of FIG. 8.

Figure 10:
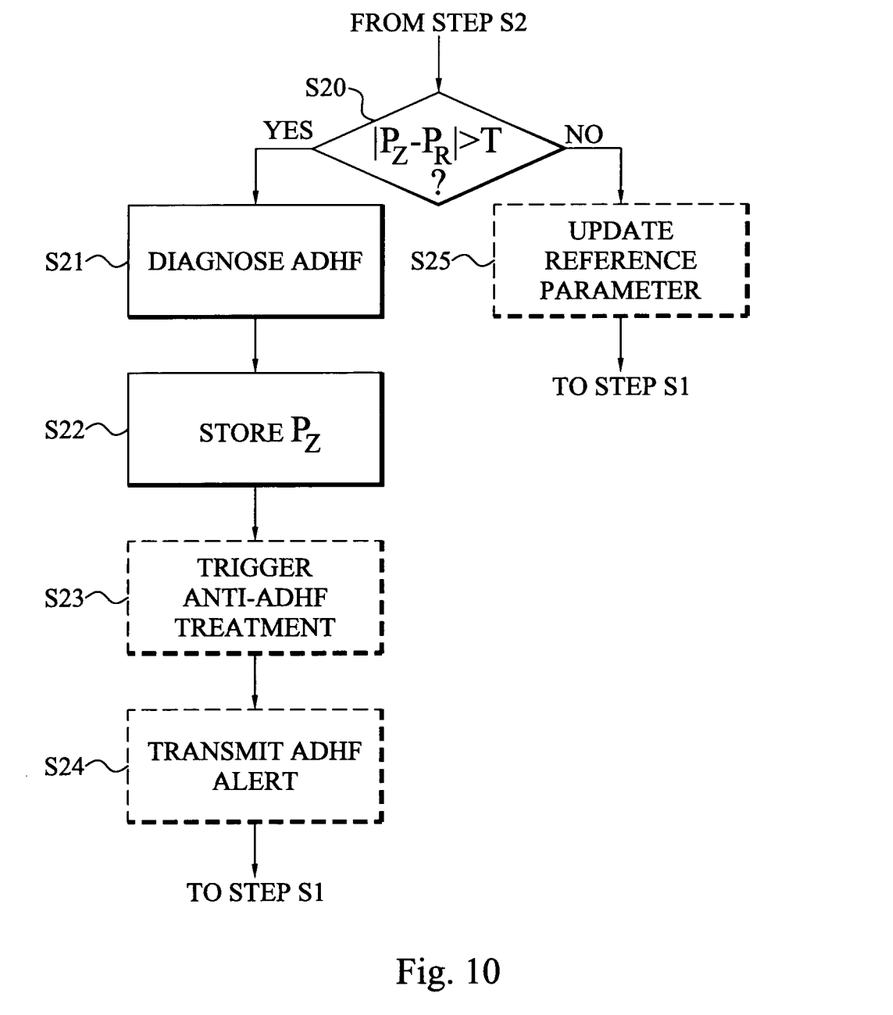
FIG. 10 is a flow diagram illustrating an embodiment of the ADHF detecting step in FIG. 8 according to a particular embodiment.

FIG. 10 is a flow diagram illustrating a preferred embodiment of the monitoring step of FIG. 8. The method continues from step S2 in FIG. 8. A next step S20 calculates a difference, preferably the absolute value of the difference, between the impedance parameter $P_Z$ and a reference parameter $P_R$. If this difference is larger than a predefined threshold T, the method continues to step S21, where ADHF is diagnosed. In order to increase the reliability in the ADHF detection, ADHF is diagnosed first when multiple such impedance parameters originating from different time instances significantly diverge from the reference parameter.

A next step S22 stores the divergent impedance parameter for later diagnostic use by a physician. The optional step S23 triggers upon confirmed detection of ADHF an anti-ADHF treatment by providing stimulating pulses according to a defined anti-ADHF scheme to the subject's heart. In addition or alternatively, an ADHF alert message may be generated and transmitted to a physician or a handheld communications terminal of the subject in step S24. The method then continues to step S1 of FIG. 8.

If ADHF is not present as determined in step S20, the method continues to step S25, where the optional step S25 updates the reference parameter $P_R$ based on the calculated impedance parameter $P_Z$ to get an updated reference parameter $P_R'$. The method continues to step S1 of FIG. 8.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable medical device comprising:
   an electrode connecting arrangement connectable to at least two electrodes;
   an impedance determiner that determines an impedance signal associated with a heart of a subject over at least a diastolic phase of a heart beat based on electric signals sensed by said at least two electrodes;
   a signal analyzer configured to identify a global maximum in said impedance signal during said heart beat, and to identify first local maximum in said impedance signal during the diastolic phase following the identified global maximum in the impedance signal;
   a parameter calculator that calculates, based on said impedance signal, an impedance parameter by applying a non-zero first weight to a diastolic portion of said impedance signal corresponding to a portion of said diastolic phase immediately preceding said identified first local maximum and up to directly following said identified first local maximum and applying a second weight to a non-diastolic portion of said impedance signal corresponding to a non-diastolic phase of said heart beat, said first weight being larger than said second weight; and an acute decompensated heart failure, ADHF, monitor that monitors an ADHF status based on said impedance parameter.

2. The implantable medical device according to claim 1, wherein said electrode connecting arrangement is connectable to at least one implantable electric lead comprising said at least two electrodes and is attachable to said heart.

3. The implantable medical device according to claim 1, wherein said parameter calculator calculates, based on said impedance signal, a diastolic impedance parameter representative of said impedance associated with said heart during at least a portion of said diastolic phase.

4. The implantable medical device according to claim 1, wherein said parameter calculator performs an isolated impedance analysis of said impedance signal during said at least a portion of said diastolic phase to calculate said impedance parameter.

5. The implantable medical device according to claim 1, wherein said second weight is zero.

6. The implantable medical device according to claim 1, wherein said impedance determiner determines said impedance signal as an average of multiple cardiogenic impedances measured during different heart beats.

7. The implantable medical device according to claim 1, further comprising:
   a signal applier that applies, through said at least two electrodes, a current signal or a voltage signal to at least a portion of said heart during at least said diastolic phase of said heart beat; and
   a signal measurer that measures a resulting voltage signal or a resulting current signal sensed by said at least two electrodes over at least a portion of said heart during at least said diastolic phase of said heart beat, said impedance determiner calculating said impedance signal based on said current signal and said resulting voltage signal or said voltage signal and said resulting current signal.

8. The implantable medical device according to claim 1, wherein said parameter calculator is calculates, based on said impedance signal, said impedance parameter by applying said non-zero first weight to a diastolic portion of said impedance signal corresponding to the portion of said diastolic phase following closure of the aortic valve up to atrial contraction and applying said second weight to said non-diastolic portion of said impedance signal.

9. The implantable medical device according to claim 1, wherein said parameter calculator calculates, based on said impedance signal, said impedance parameter by applying said non-zero first weight to a diastolic portion of said impedance signal corresponding to the portion of said diastolic phase consisting of isometric relaxation and rapid filling of the ventricles of said heart and applying said second weight to said non-diastolic portion of said impedance signal.

10. The implantable medical device according to claim 1, wherein said parameter calculator calculates said impedance parameter as representative of a time difference between the occurrence of said global maximum and said first local maximum.

11. The implantable medical device according to claim 1, wherein said parameter calculator calculates said impedance parameter as representative of an amplitude difference between said global maximum and said first local maximum.

12. The implantable medical device according to claim 1, further comprising: an electrocardiogram calculator determines an electrocardiogram signal based on electric signals collected by an electrode of said at least two electrodes; and a signal analyzer that determines, based on said electrocardiogram signal, a timing of a QRS complex during said heart beat.

13. The implantable medical device according to claim 1, further comprising a signal analyzer that determines, based on said impedance signal, a timing of a QRS complex during said heart beat.

14. The implantable medical device according to claim 12, wherein said parameter calculator calculates, based on said impedance signal, said impedance parameter by applying said non-zero first weight to a diastolic portion of said impedance signal corresponding to the portion of said diastolic phase starting about 400 ms from said timing of said QRS complex and applying said second weight to said non-diastolic portion of said impedance signal.

15. The implantable medical device according to claim 1, wherein said parameter calculator calculates said impedance parameter as representative of an area under an impedance curve obtained from said impedance signal, during said at least a portion of said diastolic phase.

16. The implantable medical device according to claim 1, wherein said parameter calculator calculates said impedance parameter as representative of a length of an impedance curve obtained from said impedance signal, during said at least a portion of said diastolic phase.

17. The implantable medical device according to claim 1, wherein said ADHF monitor comprises and an ADHF detector that detects ADHF based on said impedance parameter.

18. The implantable medical device according to claim 17, wherein said ADHF detector detects ADHF based on a comparison of said impedance parameter with a reference parameter.

19. The implantable medical device according to claim 18, wherein said parameter calculator calculates said reference parameter, based on a previously determined impedance signal, by applying said non-zero first weight to a diastolic portion of said previously determined impedance signal corresponding to at least a portion of said diastolic phase during a previous heart beat and applying said second weight to a non-diastolic portion of said previously determined impedance signal corresponding to a non-diastolic phase of said previous heart beat.

20. The implantable medical device according to claim 18, wherein said ADHF detector compares said impedance parameter with said reference parameter, and detects ADHF when a difference between said impedance parameter and said reference parameter exceeds a threshold.

21. The implantable medical device according to claim 20, further comprising a parameter updater that updates said reference parameter when said difference between said impedance parameter and said reference parameter does not exceed said threshold.

22. The implantable medical device according to claim 1, wherein said ADHF monitor monitors a recovery status from an ADHF event based on said impedance parameter.

23. An implantable medical device as claimed in claim 12 further comprising a signal analyzer that identifies a first local maximum in said impedance signal in said diastolic phase, and wherein said parameter calculator calculates said impedance parameter as representative of a time difference between occurrence of said QRS complex and said first local maximum.

24. An implantable medical device as claimed in claim 13 further comprising a signal analyzer that identifies a first local maximum in said impedance signal in said diastolic phase, and wherein said parameter calculator calculates said impedance parameter as representative of a time difference between occurrence of said QRS complex and said first local maximum.

* * * * *